United States Patent [19]

Muller et al.

[11] Patent Number: 5,486,696
[45] Date of Patent: Jan. 23, 1996

[54] PROCEDURE AND APPARATUS FOR THE ANALYSIS OF SURFACE AND/OR DEPTH PROFILES

[75] Inventors: Karl-Heinz Muller, Werne; Hans Oechsner, Kaiserslautern, both of Germany

[73] Assignee: SPECS Gesellschaft fur Oberflachenanalvtik and Computertechnologie mbH, Germany

[21] Appl. No.: 90,109

[22] PCT Filed: Jan. 14, 1992

[86] PCT No.: PCT/EP92/00067

§ 371 Date: Mar. 9, 1994

§ 102(e) Date: Mar. 9, 1994

[87] PCT Pub. No.: WO92/13268

PCT Pub. Date: Aug. 6, 1992

[30] Foreign Application Priority Data

Jan. 15, 1991 [DE] Germany .......................... 41 00 980.0

[51] Int. Cl.$^6$ .................................................. H01J 49/14
[52] U.S. Cl. .......................................... 250/288; 250/282
[58] Field of Search ............................ 250/288, 288 A, 250/281, 282, 251, 309

[56] References Cited

U.S. PATENT DOCUMENTS 4,670,651  6/1987  Meier et al. .................. 250/309
4,734,579  3/1988  Lucatorto et al. ............ 250/288
4,968,888  11/1990 Appelhans et al. ........... 250/306

FOREIGN PATENT DOCUMENTS 0296920  12/1988  European Pat. Off. .
2950330   6/1981  Germany .

Primary Examiner—Jack I. Berman
Assistant Examiner—Kiet T. Nguyen
Attorney, Agent, or Firm—Harris Beach & Wilcox

[57] ABSTRACT

The invention relates to a procedure for the analysis of surface and depth profiles of partially or completely electrically non-conductive specimens using the direct bombardment method of the secondary neutral-particle mass spectrometry SNMS; to dissipate otherwise disturbing ion currents, it is being suggested that a high-frequency alternating voltage is applied to the underside of the specimen, the upperside of which is in contact with the low-pressure plasma used in the SNMS procedure, whereby the phase of this voltage is adjusted to such a time sequence that during the negative voltage part of the high-frequency period the specimen is bombarded by positive ions of a constant kinetic energy from the plasma and that the applied ion charge from the influx of plasma electrons is compensated during the positive part of the high-frequency period.

8 Claims, 3 Drawing Sheets

PROCEDURE AND APPARATUS FOR THE ANALYSIS OF SURFACE AND/OR DEPTH PROFILES

BACKGROUND OF THE INVENTION

1. Field of the Invention

This invention relates to mass spectrometry. More particularly this invention relates to secondary neutral-particle mass spectrometry.

2. Description of the Invention

In the known procedures concerned with the secondary neutral-particle mass spectrometry, SNMS, neutral atoms and molecules are released from the surface of a solid body by ion bombardment, are ionized by the electron components of a low-pressure gas-discharge plasma and are then analyzed by a mass spectrometer. In an especially advantageous design of SNMS, ions from the ionizing plasma are accelerated in accordance with the direct bombardment technique toward the specimen by which method, in conjunction with an extremely planar adjustment of the equal potential planes in the ion acceleration path between plasma and specimen, a laterally highly homogeneous ion bombardment of the specimen surface can be achieved. If by lowering the voltage between the specimen and a reference electrode in the plasma, the ion energy is reduced to values around 100 eV any of the atomic mixing processes in the specimen typical for higher energies can almost completely be avoided. When employed for determining deep profiles of concentrations, this method, in conjunction with a laterally highly homogeneous ion removal, yields an extremely high depth resolution in the order of less than 1 nm.

These methods characteristic of the direct bombardment method of SNMS could, so far, be employed only on specimens whose electric conductivity was sufficiently high such that a dissipation of the imposed ion bombardment current could occur. It is the objective of the present invention to enable using this method also on completely or partially electrically non-conducive specimens.

SUMMARY OF THE INVENTION

The invention is based on the following principle:

When a negative voltage is applied to the underside of an isolating specimen or of a specimen that is mounted on an isolating surface (see (1) in FIG. 1a), this same voltage will also appear at the topside of the specimen through electrostatic induction. If the specimen is located within a plasma, the constant ion saturation current flowing onto the specimen will compensate this surface voltage until the floating voltage is reached (FIG. 1b). During this 'discharge time', $\Delta t_1$, the specimen is bombarded by ions with ever decreasing energy. The determining factors of $\Delta t_1$ are the specimen's capacity and the ion saturation current.

When a positive voltage is applied to the specimen (see (2) in FIG. 1a) the process described above repeats itself, now, however, with electrons flowing onto the specimen instead of ions. The corresponding 'discharge time' $\Delta t_2$ is shorter than $\Delta t_1$ due to the comparatively much higher electron current (FIG. 1b).

If, instead, a rectangular-wave alternating voltage is applied with a frequency where the discharge time is large compared to the duration of the negative half period, the specimen surface cannot discharge itself during the negative half period (FIG. 2). During this period the specimen is bombarded by highly monoenergetic ions and, thereby, eroded (sputtering). The length ratio depends on the requirements of the corresponding analyses. It lies between 1 to $10^2$ and 1 to $10^5$ and is typically (normal case) 1 to $10^3$.

By choosing a proper ratio of the positive voltage phase duration to the negative voltage phase duration, $\Delta T(-):\Delta T(+)$ in the high-frequency period T (FIG. 2), the portion of T during which the specimen is bombarded by ions and which, therefore, is equal to the duration of analysis or the counting rate for the mass-spectrometric signals, can be optimized. The requirement always remains that $\Delta_1$ has to remain large in comparison to $\Delta T(-)$. $\Delta T(+)$ may be shortened to as low as $\Delta t_2$.

With the method described, the 'direct bombardment mode (DBM)' of SNMS, formerly applicable only to electrically conductive specimens, can now also be applied to the analysis of dielectric specimens (isolators). By choosing the proper distance between the focusing orifice and the specimen, a laterally homogeneous erosion of the specimen can be achieved since, during the negative half period in tho ion bombardment phase, ion-optical conditions are achieved that are similar to the DBM of electrically conductive specimens. At small amplitudes of the rectangular-wave high-frequency alternating voltage, i.e. at low negative specimen voltages and, correspondingly, low ion bombardment energies, the same conditions are now achieved for dielectric specimens where the DBM on electrically conductive specimens leads to an extremely high depth resolution. An example of this is shown in FIG. 3.

In one aspect of the invention the high-frequency alternating voltage has a rectangular wave shape such that, during the ion bombardment phase, a constant bombardment voltage is applied to the specimen (1) thus enabling ion-optical adjustments to achieve a laterally homogeneous erosion of the specimen (1) by ion bombardment.

In another aspect of the invention the positive portion $\Delta T(+)$, of the high-frequency voltage is about equal to the electron discharge time, $\Delta t_2$.

In yet another aspect of the invention the amplitude of the high-frequency voltage can be reduced down to below 100 V such that a high depth resolution can be achieved.

BRIEF DESCRIPTION OF THE DRAWING

The invention is described on the basis of FIGS. 1 through 4.

DESCRIPTION OF THE PREFERRED EMBODIMENT

Figure 1A:
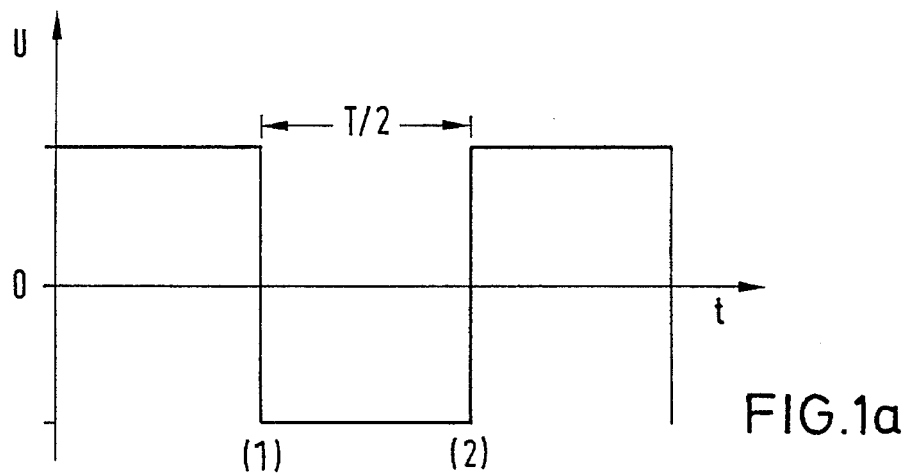
FIG. 1a illustrates a time sequence of the rectangular-wave alternating voltage on the underside of the specimen.
Figure 1B:
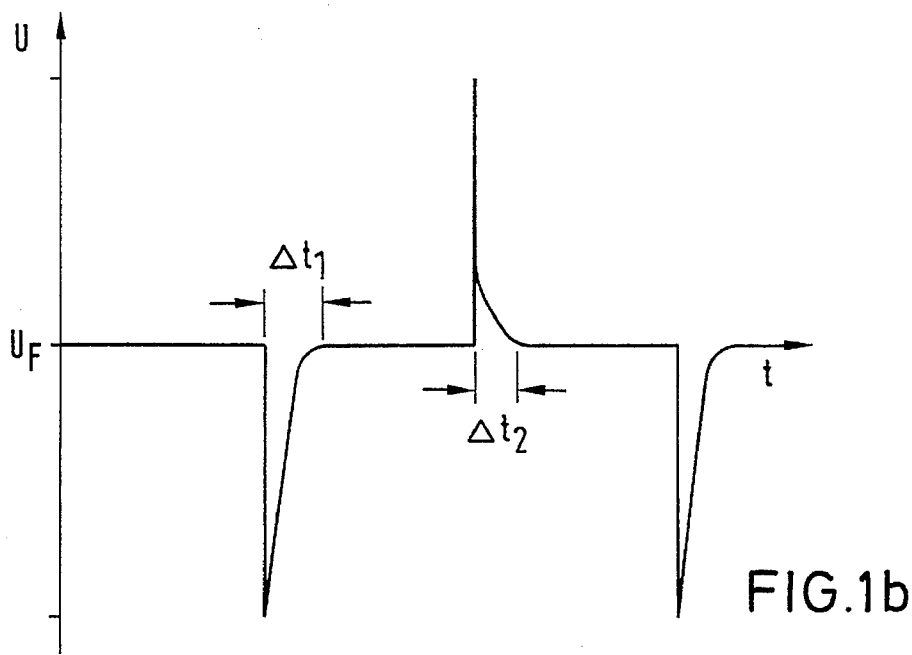
FIG. 1b: shows a time sequence of the voltage on the specimen surface. The duration of a single half-period is larger than the 'discharge times', $\Delta t_1$ and $\Delta t_2$.
Figure 2:
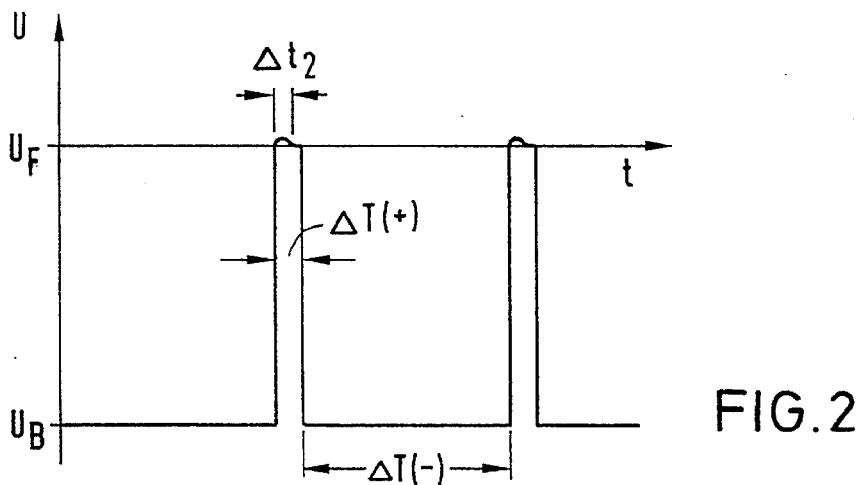
FIG. 2 shows a time sequence off the voltage on the specimen surface in the case that the negative portion $\Delta T(-)$, of the high-frequency voltage is very small compared to the ion discharge time, $\Delta t_1$ (FIG. 1), and that $\Delta T(+)$ is comparable to the electron discharge time, $\Delta t_2$.
Figure 3:
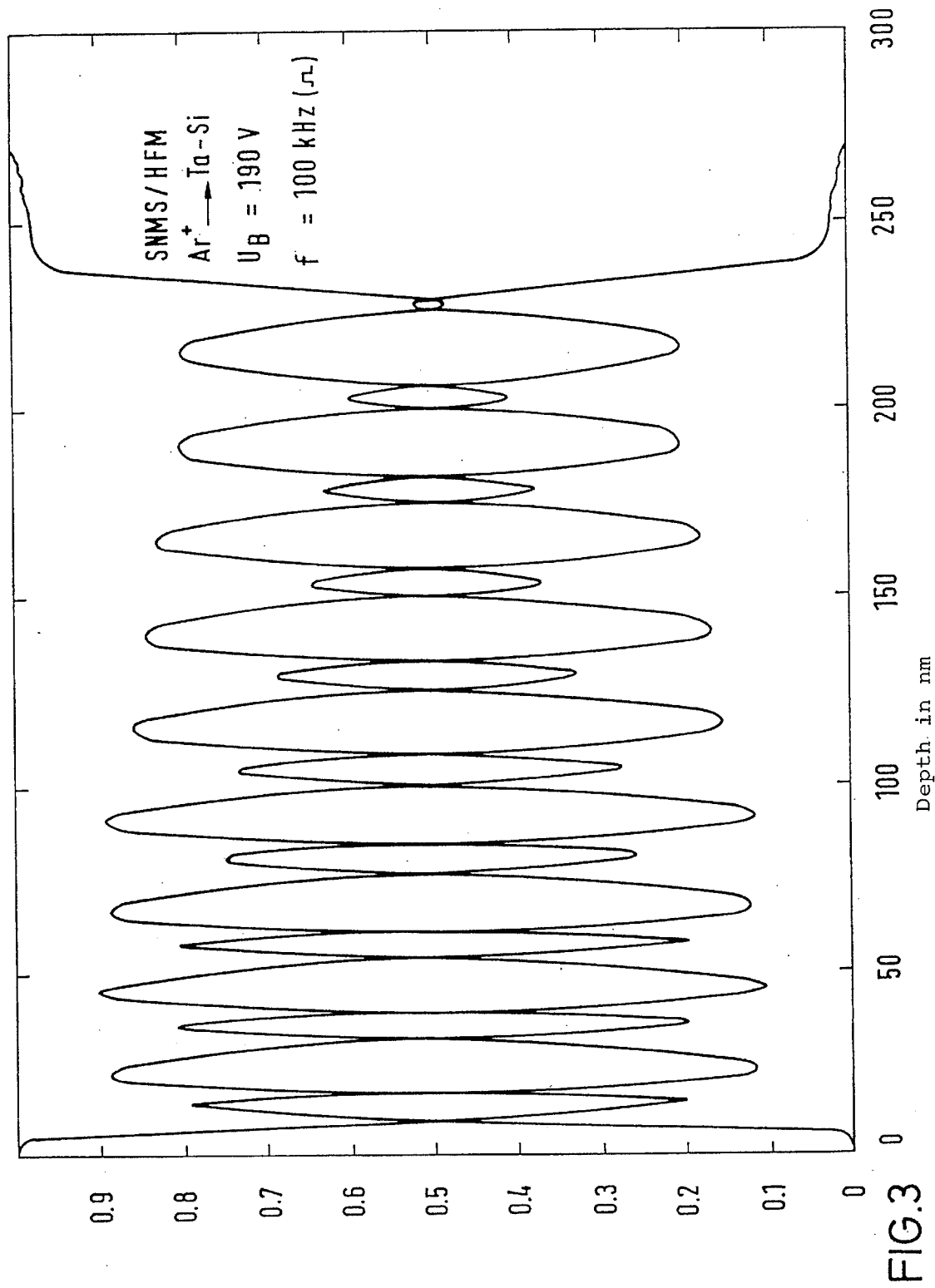
FIG.3 illustrates a concentration depth profile of a TaSi multi-layered system (double layer thickness d=20 nm) determined by the SNMS high-frequency method. In this measurement the multi-layered system—itself being a conductor—was mounted on an electrically isolating specimen holder. The frequency of the rectangular voltage employed was 100 kHz. During the negative half period the specimen was bombarded by 190 eV Ar$^+$ ions in a direction perpendicular to the specimen surface.
Figure 4:
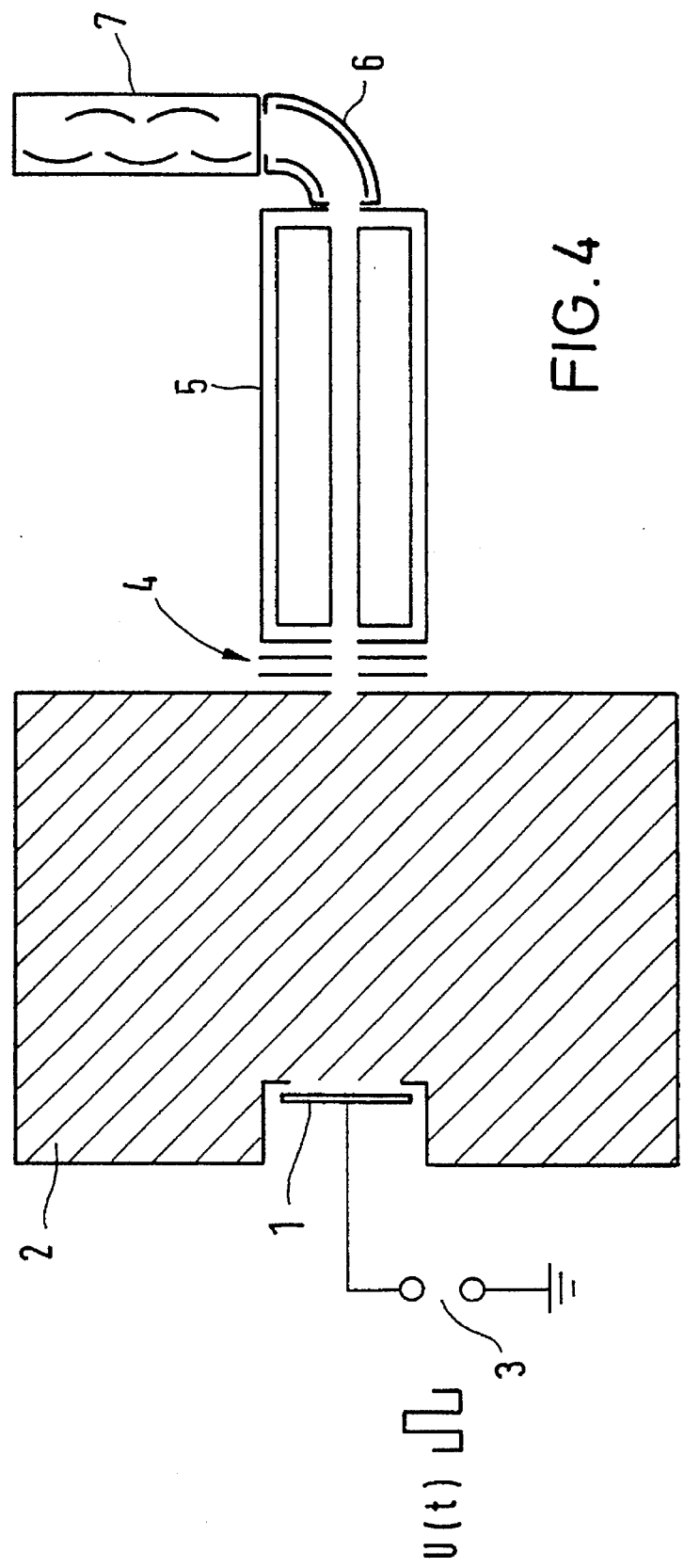
FIG. 4 is a schematic drawing of an SNMS device for performing analyses by the high-frequency method (see also DE-A-29 50 330). Located on the side of the plasma 2 and opposite to the specimen 1 are an electron-optical arrangement 4, a quadrupole mass-spectrometer 5, a beam diversion unit 6 as well as a secondary electron-multiplier tube 7.

The apparatus required for the SNMS analysis with the high-frequency method is identical to the SNMS/DBM design except for the one modification of requiring a lead-in for the bombardment voltage which is necessary for applying the high-frequency voltage (FIG. 4). The specimen 1 to be analyzed is in direct contact with the plasma 2. In accordance with this invention, a rectangular wave high-frequency voltage is applied to the underside of the specimen 1, the voltage being created by an adjustable frequency rectangular-wave voltage generator 3 whose voltage amplitude can be adjusted between 0 and several kV. By chosing the proper frequency and amplitude a defined-bombardment energy can be achieved. The frequency must be so adjusted that no discharge worth mentioning occurs during the negative period ($\Delta T(-)$, see above). With this prerequisite fulfilled, a monoenergetic bombardment of the specimen is assured. The voltage on the surface of the specimen is determined with a measurement probe (not shown in FIG. 4) in order to enable a fine adjustment, if so required. This can be important in the depth profile analysis and in the analysis of thin-layered systems where, in the course of sputtering (i.e with growing depth), a change of capacity occurs. The measurement probe could be designed as a capacitative or inductive pickup or as a fine-point contact probo.

So far there is no known apparatus that combines high-frequency sputtering with the secondary neutral particle mass-spectrometry. When applying high-frequency sputtering to isolators in plasmas one generally uses sinusoidal alternating voltages in the MHz range. The essential aspect of the present patent application is the use of a rectangular-wave alternating voltage. This is prerequisite for achieving a monoenergetic bombardment energy together with a homogeneous specimen erosion in the case dielectric specimens.

Even if a high-frequency sinusoidal voltage in the order of 10 MHz is used which generally leads to a homogenisation of the bombardment energy, this still would not achieve the necessary homogenisation of the bombardment current required for a high depth resolution since a periodically changing surface voltage also leads to a periodically changing depth of the space charge over the specimen. However, to achieve homogeneous specimen erosion a well defined time-constant relationship between the voltage difference between specimen surface and plasma, the depth of the space charge layer.

We claim:

1. Procedure for analyzing the surface and/or depth profile of specimens, said specimens being completely or partially electrically non conductive, employing the direct bombardment method of the secondary neutral-particle mass spectrometry SNMS, comprising the steps of:

applying a high-frequency alternating voltage to an underside of a specimen, said specimen having an upperside in direct contact with a low-pressure plasma; wherein said alternating voltage has high frequency periods wherein, during negative voltage phases of said high-frequency periods, said upperside of said specimen is bombarded by positive ions from said plasma with a constant kinetic energy for producing neutral atoms and molecules and, during positive voltage phases of said high-frequency periods, said upperside of said specimen is bombarded by electrons from said plasma for compensating the charge produced on said specimen by said positive ions.

2. Procedure in accordance with claim 1 further comprising the steps of:

ionizing said neutral atoms and molecules in said plasma; and analyzing said ionized atoms and molecules in a mass spectrometer.

3. Procedure in accordance with claim 1 or 2 wherein the high-frequency alternating voltage has a rectangular wave shape such that, during the ion bombardment phase, a constant bombardment voltage is applied to the specimen thus enabling ion-optical adjustments to achieve a laterally homogeneous erosion of the specimen by ion bombardment.

4. Procedure in accordance with claim 3 wherein the negative portion $\Delta T(-)$, of the high-frequency voltage is very small compared to the ion discharge time.

5. Procedure in accordance with claim 3 wherein the positive portion $\Delta T(+)$, of the high-frequency voltage is about equal to the electron discharge time, $\Delta t_2$.

6. Procedure in accordance with claim 1 wherein an amplitude of the high-frequency voltage is less than 100 V whereby a high depth resolution is achieved.

7. Procedure in accordance with claim 1, wherein a ratio between the negative and the positive voltage phase of the high-frequency period is selected, whereby a laterally homogeneous ion bombardment is achieved over as long a part of the high-frequency period as possible.

8. Procedure in accordance with claim 1 wherein the underside of the specimen, is connected to a generator which creates a rectangular-wave voltage.

* * * * *